United States Patent [19]

Atkinson et al.

[11] Patent Number: 5,152,746

[45] Date of Patent: Oct. 6, 1992

[54] LOW PRESSURE IRRIGATION SYSTEM

[75] Inventors: Robert W. Atkinson, Dover; Michael J. Laco, Sherrodsville, both of Ohio

[73] Assignee: Zimmer, Inc., Warsaw, Ind.

[21] Appl. No.: 516,933

[22] Filed: Apr. 30, 1990

[51] Int. Cl.⁵ .............................................. A61M 1/00
[52] U.S. Cl. ....................................... 604/31; 604/33; 604/66; 604/67; 604/245; 604/249
[58] Field of Search .................. 604/246, 247, 30, 31, 604/33, 34, 50, 51, 118, 123, 65-66, 28, 80, 249, 131, 245, 152; 137/557; 116/70, 268, 270; 417/218, 222, 212, 213

[56] References Cited

U.S. PATENT DOCUMENTS

| | | | |
|---|---|---|---|
| 3,358,677 | 12/1967 | Sheldon | 128/24 AA |
| 3,900,022 | 8/1975 | Widran | 604/31 |
| 4,258,721 | 3/1981 | Parent | 604/26 |
| 4,650,462 | 3/1987 | De Satnick | 604/30 |
| 4,795,424 | 1/1989 | Burner | 604/30 |
| 4,820,265 | 4/1989 | De Satnick et al. | 604/30 |
| 4,876,788 | 10/1989 | Steer et al. | 29/508 |
| 4,940,457 | 7/1990 | Olson | 604/247 |
| 4,994,035 | 2/1991 | Mokros | 604/118 |
| 4,998,527 | 3/1991 | Meyer | 128/6 |
| 4,998,914 | 3/1991 | Wiest | 604/67 |

OTHER PUBLICATIONS

Ewing et al, Intra-Articular Pressures During Arthroscopic Knee Surgery, The Journal of Arthroscopic and Related Surgery 2(4): 264–269, 1986.

Primary Examiner—C. Fred Rosenbaum
Assistant Examiner—Mark Bockelman
Attorney, Agent, or Firm—Paul David Schoenle

[57] ABSTRACT

An irrigation system is provided to communicate fluid pressure to a body cavity for diagnostic or surgical proceedings. A pump control unit generates fluid pressure and a monitor control circuit provides feedback to the pump control unit to substantially avoid a build up of excessive fluid pressure within the body cavity. In combination with a hysterscope, the irrigation system extends a uterus in a safe manner so that fluid absorption within the uterus is substantially eliminated.

8 Claims, 2 Drawing Sheets

LOW PRESSURE IRRIGATION SYSTEM

BACKGROUND OF INVENTION

The present invention relates to an irrigation system for communicating a fluid media to a body cavity.

In certain surgical and diagnostic procedures it is common to communicate a fluid media to a body cavity to pressurize the cavity. The pressurized fluid media extends or expands the cavity to provide better vision and access to tissue within the cavity via cannula extending into the body cavity. For example, in arthroscopic procedures of human joints, such as the knee joint, saline solution is communicated under pressure to the knee joint via a cannula extending into the knee joint. The pressurized saline solution within the knee joint expands the latter to improve visual inspection via an endoscope. In addition, the expanded knee joint improves accessibility via a cannula extending into the knee joint to resect torn or scarred tissue therein.

Heretofore, an injection system for arthroscopy of a joint, as illustrated in U.S. patent application Ser. No. 07/137,138, now U.S. Pat. No. 4,940,457 filed Dec. 23, 1987, included fluid tubing extending from a pump to the knee joint and a return tubing communicated the fluid pressure within the joint to the pump to provide a feed back for controlling fluid pressure communicated through the fluid tubing. In view of the sensitive nature of human tissue the fluid pressure communicated to the knee joint must be kept at a minimum fluid pressure level over a substantial length of time corresponding to an arthroscopic surgical procedure.

Apart from arthroscopic surgical procedures, gynecologist have utilized endoscopes for hysteroscopy whereby diagnostic and surgical procedures have been performed on the uterus. The uterus lining is substantially collapsed so that endoscope visual inspection is difficult; however, extension of the uterus with fluid pressure is problematic in view of the uterus connection with fallopian tubes and the absorption characteristics of the uterus lining. Fluid pressure above 100 millimeters of mercury is believed to initiate absorption of fluid within the venus sinuses of a patient's blood system.

It is common practice today to utilize a bottle of hyskon fluid in communication with the uterus and to apply pressure to the bottle of hyskon to communicate pressurized hyskon to the uterus in the absence of an adequate control for limited pressure levels within the uterus.

SUMMARY OF THE INVENTION

The present invention provides an irrigation system for communicating a first fluid media to a body cavity comprising means for communicating the first fluid media to the body cavity via a cannula extending into the body cavity, the communicating means including a pump control unit to pressurize the first fluid media and first fluid tubing extending from the pump control unit to the cannula, and a monitor control circuit extending from the cannula to the pump control unit to communicate fluid pressure associated with the cannula to the pump control unit, the monitor control circuit including a second fluid media different from the first fluid media but responsive to the fluid pressure of the first fluid media to assist the pump control unit in maintaining a predetermined fluid pressure level for the first fluid media within the body cavity.

In a specific application of the present invention an irrigation system is provided for extension of a body cavity, such as a uterus, wherein the pump control unit communicates fluid pressure to the endoscope via tubing. The endoscope extends into the uterus and the monitor control circuit extends from the endoscope to the pump control unit to assist the latter in maintaining a safe fluid pressure level within the uterus.

The first fluid media is a highly viscous fluid below ten (10) centipods. Examples of such a fluid are Sorbital, Ringers Lactate, or Glycine.

It is the object of the present invention to provide an irrigation system communicating fluid pressure to a body cavity with safeguards in the system limiting the maximum pressure level communicated to the body cavity.

It is a further object of the invention to utilize two fluid media for respectively communicating fluid pressure to the body cavity and providing a feed back indication of the fluid pressure level within the body cavity to the pump control unit.

In another aspect of the invention a compact housing is provided with the irrigation system to define a diaphragm separating the two fluid media and a relief valve limiting the maximum pressure communicated to the body cavity as well as absorbing fluctuations in the fluid pressure generated by the pump control unit.

Figure 1:
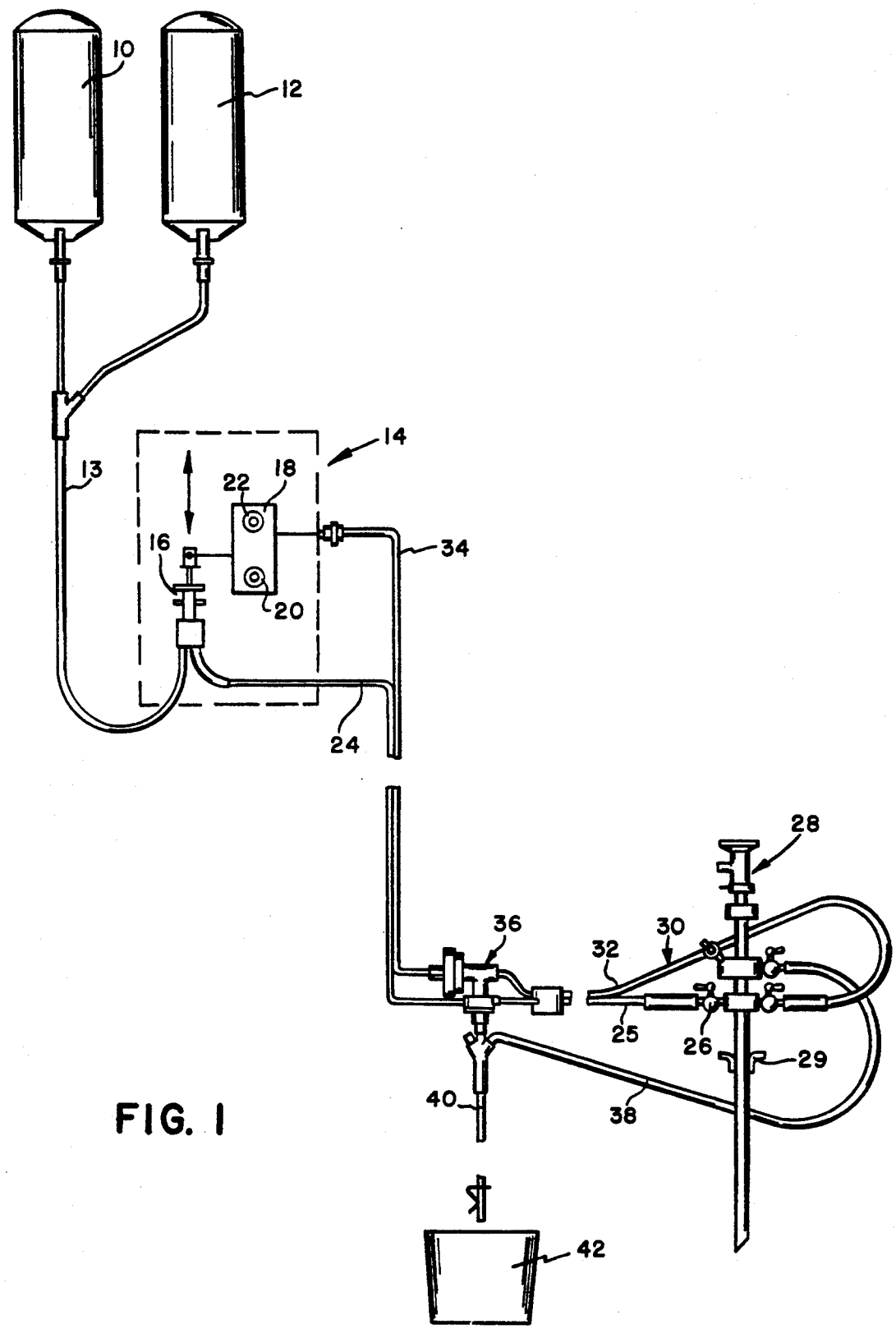
FIG. 1 is a schematic illustration of the irrigation system of the present invention.

The irrigation system of FIG. 1 includes a pair of fluid bags 10 and 12 containing a highly viscous liquid, such as Sorbital, Ringers Lactate, or Glycine. The pair of bags 10 and 12 communicate via tubing 13 with a pump control unit 14 schematically illustrated as a piston pump 16 and controller 18. Dials 20 and 22 or other suitable switches, are provided on the controller 18 to adjust the fluid pressure level and fluid flow desired by an operator. Fluid tubing 24 and 25 extends from the output of the piston pump 16 to an inlet port 26 on an endoscope 28 commonly referred to as a hysteroscope. A monitor control circuit 30 includes a second fluid tubing 32 and a third fluid tubing 34 that are joined at a common housing 36. As described in more detail hereinafter, the third fluid tubing 34 includes trapped air. The second fluid tubing 32 extends from the endoscope 28 to the common housing 36 and the third fluid tubing 34 extends from the common housing 36 to the controller 18 of the pump control unit. An outlet tubing 38 extends from the endoscope 28 to the common housing 36 to communicate with a drain tube 40 emptying into a container 42.

Figures 2, 3:
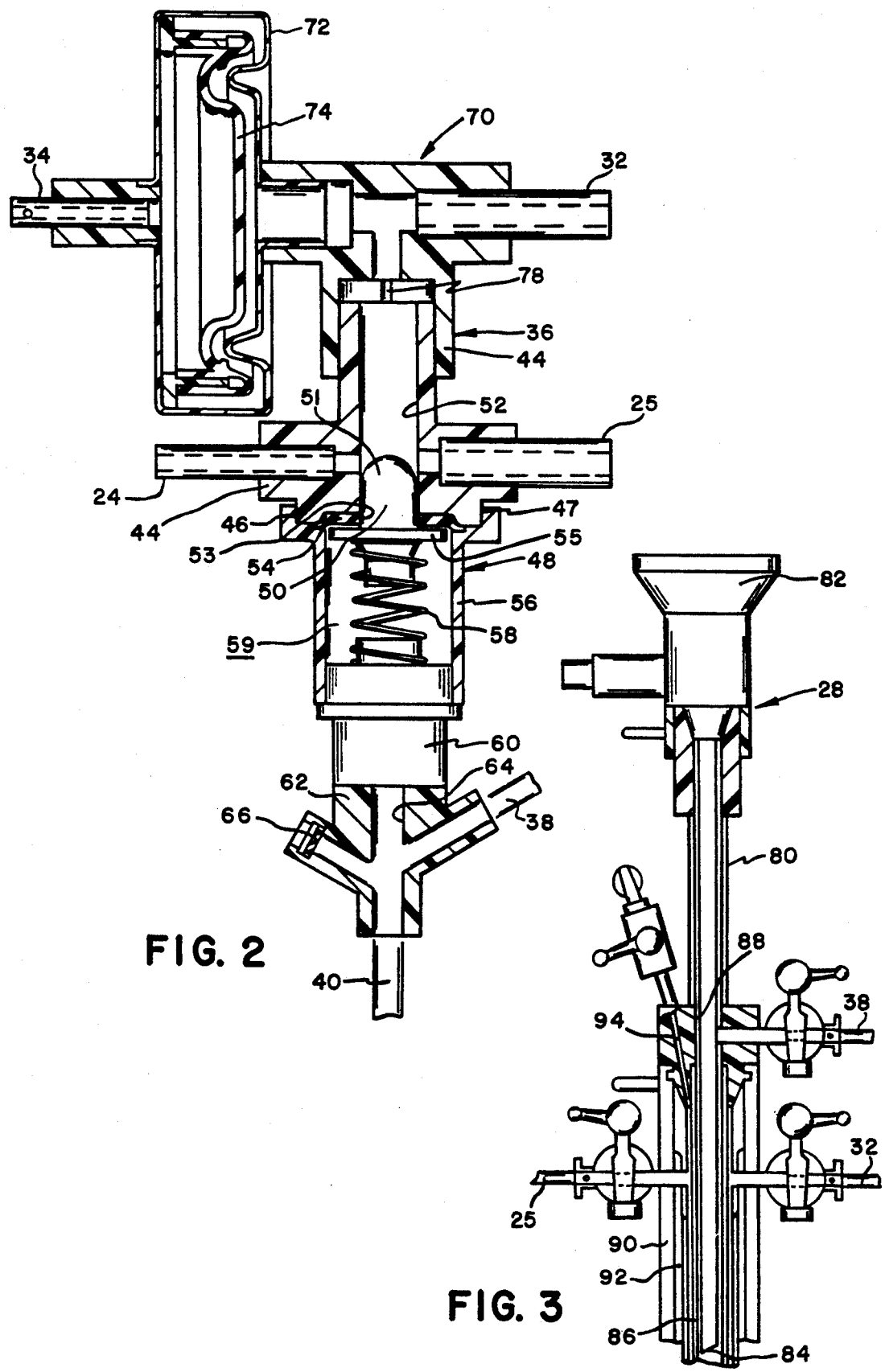
FIG. 2 is a cross sectional view of the common housing within the irrigation system of FIG. 1.
FIG. 3 is a cross sectional view of the endoscope illustrated in FIG. 1.

Turning to FIG. 2 the common housing 36 includes a plurality of fittings 44 to connect with tubing 24, 25, 32, 34, 38 and 40. The lower portion 46 of the housing 36 defines an enlarged circular base 47 carrying a relief valve assembly 48. The relief valve assembly 48 includes a poppet 50 extending into a passage 52 in communication with tubing 24 and 25, and a resilient seat 54 trapped at its periphery between the enlarged base 47 and a relief valve assembly cap 56 secured to the enlarged base 47. The cap 56 supports a spring 58 within a chamber 59 biasing the poppet 50 toward the passage 52. The poppet 50 forms a dome 51 extending through an opening 53 in the resilient seat 54. The dome 51 terminates in a flange 55 opposing spring 59 and resilient seat 54. Although the flange 55 is illustrated in spaced relation to the resilient seat 54, the flange 55 usually engages the resilient seat 54 to establish a seal therebetween.

A connector 60 is secured to the cap 56 and the connector carries a support 62 connected to the outlet tubing 38 and the drain tube 40. The support 62 includes a bore 64 communicating with the chamber 59, the outlet tubing 38 and the drain tubing 40. In addition, the support 62 carries a check valve 66 permitting communication of atmospheric air to the bore 64 whenever the fluid pressure within the bore 64 is lower than atmospheric pressure.

The upper portion 70 of the common housing 36 adjacent tubing 32 and 34 defines an enlarged casing 72 supporting a diaphragm 74 therein. The diaphragm 74 is exposed to fluid pressure within the tubing 32 and the tubing 34 and sealingly engages the casing 72 to isolate fluid within tubing 32 from the fluid within tubing 34. The tubing 32 is in communication with the liquid contained within the bags 10 and 12, while the tubing 34 includes trapped air extending from the diaphragm to the controller.

The common housing 36 includes a restricted orifice 78 permitting restricted fluid communication between tubing 24 and 25 and tubing 32 via passage 52. If the tubing 25 or 32 is occluded, fluid pressure from the tubing 24 is communicated through the restricted orifice 78 to activate the diaphragm 74 and thus the controller 18 to control the pump 16.

Turning to FIG. 3, the endoscope 28 includes a telescope 80 extending from an eyepiece 82 to a distal tip 84. An inner cannula 86 cooperates with the telescope 80 to define an annular passage 88 extending to the distal tip and communicating with the outlet tubing 38. An outer cannula 90 cooperates with the inner cannula 86 to define an inlet path 92 leading to the distal tip 84 and communicating with the tubing 25 and 32. An instrument port 94 is provided at the end of the outer cannula 90 to intersect the inlet path 92 so that an instrument, such as a laser, can be inserted through the inlet path to extend outwardly from the distal tip 84.

In operation, the tubing 25, 32 and 38 are connected to the endoscope and the fluid bags 10 and 12 are connected to the tubing 13. The drain tube 40 is coupled to the container 42 and the endoscope 28 is inserted into the body cavity to be examined and/or surgically treated. With the endoscope 28 extending into a uterus, a seal 29 is used to substantially eliminate flow of fluid between the endoscope and an opening heading to the body cavity. As a result most if not all of the fluid drains from the body cavity through the outlet tubing 38. In order to expand the body cavity and improve visual observation via the telescope 80, the operator sets the dials 20 and 22 of the controller 18 to the appropriate fluid pressure level and fluid flow. If the body cavity is a uterus, the fluid pressure level is set at about 80 millimeters of mercury and the flow rate is set to the required need of the out flow, up to 350 ml/min. With the controller activated at the aforegoing fluid pressure level and flow rate, the piston pump 16 is activated to communicate fluid pressure through tubing 24, common housing 36, tubing 25 and inlet path 92 to the distal tip 84 which has been inserted into the uterus. Fluid pressure within the uterus causes the latter to expand to improve vision within the uterus via the telescope 80. The fluid pressure within the inlet path 92 is also communicated to the tubing 32 and into common housing 36 to bias the diaphragm to move toward tubing 34. With air trapped between the controller 18 and the diaphragm 74, the force of fluid pressure from tubing 32 acting against the diaphragm 74 compresses the air in tubing 34 to generate a feed back response to the controller which is directly related to the fluid pressure within the inlet path 92 and the uterus. In addition, fluid pressure within the uterus is communicated to the annular passage 88 nd out the outlet tube 38 co the drain tube 40 and container 42. If the fluid pressure level within the uterus falls below the desired setting, reduced fluid pressure acting against the diaphragm 74 reduces the compression of air in tubing 34 so that the feedback signal automatically increases the amplitude of operation or stroke length for the piston pump to increase fluid communication to the uterus via tubing 24 and 25. Similarly, an increase in the fluid pressure within the uterus above a desired safe setting increases fluid pressure acting against the diaphragm to further compress the air trapped in tubing 34 so that the feedback signal to the controller automatically decreases the amplitude or stroke length of operation for the piston pump to reduce fluid communication to the uterus.

With increasing fluid pressure the poppet 50 is movable with the valve seat until a maximum desired level is reached. At the maximum desired level, the poppet separates from the movable valve seat to open tubing 24 and 25 to the drain tubing 40 via cap chamber 59 and support bore 64. Any fluctuation in fluid pressure below the maximum desired level will cause the poppet and seat to modulate thereby dampening fluid pressure oscillations communicated to tubing 25 to substantially avoid pressure fluctuations within the endoscope and uterus. The spring 58 is calibrated to the maximum desired pressure level and the check valve 66 allows atmospheric pressure to enter the chamber 59 in the event a negative pressure differential is established between the chamber 59 and the atmosphere.

The irrigation system of the present invention is designed with several safety features. The relief valve assembly 48 is disposed in the common housing upstream from the endoscope 28 to substantially eliminate excessive fluid pressure communication to the endoscope. The controller 18 is programmed to develop a maximum pressure level of only 80 millimeters of mercury for the piston pump 16. The air trapped within the tubing 34 of the monitor control circuit substantially eliminates any head pressure build up which would result from different elevations between the patient and common housing 36 and the pump control unit 14.

I claim:

1. An irrigation system for communicating a first fluid media to a body cavity comprising means for communicating the first fluid media to the body cavity via a cannula extending into the body cavity, the communicating means including a pump control unit with a pump and a controller to pressurize the first fluid media; first fluid tubing extending from the pump control unit to the cannula; and a monitor control circuit extending from the cannula to the pump control unit to communicate fluid pressure associated with the cannula to the pump control unit in response to which the controller modulates the pump output, the monitor control circuit including a second fluid media different from the first fluid media but responsive to the fluid pressure of the first fluid media to assist the pump control unit in maintaining a predetermined fluid pressure level for the first fluid media within the body cavity, the first fluid tubing and the monitor control circuit include a common housing, the housing including a diaphragm to separate the first fluid media from the second fluid media and a relief valve limiting the maximum fluid pressure of the first fluid media.

2. The irrigation system of claim 1 in which the monitor control circuit includes a second fluid tube communicating the first fluid media between the common housing and the cannula and a third fluid tube communicating the second fluid media between the common housing and the pump control unit.

3. The irrigation system of claim 1 in which the monitor control circuit and the first fluid tubing communicate with each other via a restricted passage formed within the common housing.

4. The irrigation system of claim 1 in which the relief valve comprises a poppet biased to a closed position and a resilient seat engageable with the poppet in the closed position, a portion of the resilient seat initially moving with the poppet in response to an increase in the fluid pressure of the first fluid media and the poppet moving relative to the portion of the resilient seat to an open position in response to further increases in the fluid pressure of the first fluid media.

5. The irrigation system of claim 1 in which the common housing includes an enlarged casing supporting the diaphragm and an enlarged base supporting the relief valve.

6. The irrigation system of claim 5 in which the relief valve defines a first surface area in communication with the first fluid media and the diaphragm defines a second surface area in communication with the first fluid media and the first surface area is smaller than the second surface area.

7. The irrigation system of claim 1 further comprising, a drain tube connected to the relief valve by a connector, and a check valve located within the connector to communicate atmospheric air to the connector whenever the fluid pressure within the connector is lower than atmospheric.

8. The irrigation system of claim 1 in which the first fluid media and the second fluid media interface at a diaphragm within the monitor control circuit and a restricted passage within the housing communicates the monitor control circuit with the first fluid tubing downstream of the diaphragm.

* * * * *